(12) United States Patent
Bogaerts (10) Patent No.: US 10,052,243 B2
(45) Date of Patent: Aug. 21, 2018

(54) DIAPER CLOSURE SYSTEM (75) Inventor: Bert Bogaerts, Boechout (BE)

(73) Assignee: Avery Dennison Corporation, Pasadena, CA (US)

( * ) Notice: Subject to any disclaimer, the term of this patent is extended or adjusted under 35 U.S.C. 154(b) by 851 days.

(21) Appl. No.: 13/876,010

(22) PCT Filed: Sep. 28, 2011

(86) PCT No.: PCT/US2011/053692
§ 371 (c)(1),
(2), (4) Date: Mar. 26, 2013

(87) PCT Pub. No.: WO2012/044688
PCT Pub. Date: Apr. 5, 2012

(65) Prior Publication Data
US 2013/0184671 A1 Jul. 18, 2013

Related U.S. Application Data

(60) Provisional application No. 61/387,174, filed on Sep. 28, 2010.

(51) Int. Cl.
*A61F 13/62* (2006.01)
*A61F 13/56* (2006.01)
*A61F 13/58* (2006.01)
*D04H 18/00* (2012.01)

(52) U.S. Cl.
CPC ........ *A61F 13/5644* (2013.01); *A61F 13/581* (2013.01); *A61F 13/622* (2013.01); *A61F 13/627* (2013.01); *D04H 18/00* (2013.01)

(58) Field of Classification Search
CPC ...... A61F 13/62; A61F 13/622; A61F 13/625; A61F 13/627; A61F 13/581; A44B 18/008; A44B 18/0084; A44B 18/0088
USPC .................................... 604/391; 24/442–452
See application file for complete search history.

(56) References Cited

U.S. PATENT DOCUMENTS

| | | | |
|---|---|---|---|
| 4,369,786 A | | 1/1983 | Miller |
| 4,795,456 A | | 1/1989 | Borgers et al. |
| 5,462,540 A | | 10/1995 | Caldwell |
| 5,599,620 A | | 2/1997 | Huskey |
| 5,614,281 A | * | 3/1997 | Jackson et al. ............... 428/100 |
| 5,624,427 A | * | 4/1997 | Bergman et al. ............. 604/391 |
| 5,660,659 A | | 8/1997 | Caldwell |
| 5,720,739 A | | 2/1998 | Nguyen et al. |
| 6,205,623 B1 | * | 3/2001 | Shepard et al. ........... 24/30.5 R |
| 6,419,667 B1 | | 7/2002 | Hartman et al. |
| 2003/0232170 A1 | * | 12/2003 | Gillette et al. .................. 428/92 |
| 2004/0158957 A1 | * | 8/2004 | Horn et al. ..................... 24/442 |

(Continued)

FOREIGN PATENT DOCUMENTS

CN 1897905 A 1/2007

OTHER PUBLICATIONS

International Search Report dated Dec. 7, 2011 for International Application No. PCT/US2011/053692 filed Sep. 28, 2011.

(Continued)

*Primary Examiner* — Lynne Anderson
(74) *Attorney, Agent, or Firm* — Avery Dennison Corporation (57) ABSTRACT

One or more fastener tabs using particular spunlace materials are described. The fastener tabs find wide application as closure systems and can be used in products such as in disposable diapers.

7 Claims, 5 Drawing Sheets (56) References Cited

U.S. PATENT DOCUMENTS

| | | | |
|---|---|---|---|
| 2004/0258902 A1* | 12/2004 | Seth et al. | 428/315.7 |
| 2005/0079321 A1 | 4/2005 | Tuman et al. | |
| 2006/0069380 A1* | 3/2006 | Chen et al. | 604/391 |
| 2006/0246256 A1* | 11/2006 | Ausen et al. | 428/100 |
| 2007/0098953 A1* | 5/2007 | Stabelfeldt et al. | 428/100 |
| 2007/0119032 A1* | 5/2007 | Efremova et al. | 24/305 |
| 2007/0172628 A1* | 7/2007 | Seth et al. | 428/85 |
| 2008/0026178 A1 | 1/2008 | Stupperich | |
| 2008/0038507 A1* | 2/2008 | Seth et al. | 428/80 |
| 2009/0068394 A1 | 3/2009 | Noelle et al. | |
| 2010/0030176 A1 | 2/2010 | Beckert et al. | |
| 2011/0160690 A1* | 6/2011 | Schoenbeck | 604/385.16 |

OTHER PUBLICATIONS

Written Opinion dated Dec. 7, 2011 for International Application No. PCT/US2011/053692 filed Sep. 28, 2011.

* cited by examiner

DIAPER CLOSURE SYSTEM

CROSS-REFERENCE TO RELATED APPLICATION

The present application is a 371 of International Application No. PCT/US2011/053692, which was published in English on Apr. 5, 2012, which claims priority to U.S. Provisional Application No. 61/387,174 filed Sep. 28, 2010, which is incorporated herein by reference in its entirety.

FIELD OF THE INVENTION

The present invention relates to an improved closure system useful for products such as disposable diapers, adult incontinence briefs, training pants, sanitary napkins and the like.

BACKGROUND OF THE INVENTION

Closure systems for disposable diapers are typically pressure sensitive adhesive fastening tape tabs that are permanently attached to corners of a diaper at one diaper end and releasably attached to a front panel region of the diaper outer face at a second opposing end of the diaper. The diaper is designed such that the adhesive fastening tape tab can be removed from the frontal region when the diaper is soiled, without tearing the diaper backsheet or destroying the adhesive properties of the diaper fastening tape tab.

Mechanical closures for diapers are also known. The mechanical closure is typically a hook and loop type mechanical fastener. The hook portion of the mechanical fastener generally is placed on the diaper at the location where the pressure-sensitive adhesive fastening tab is typically located. A mating loop section of material or region is then provided on the diaper front portion, where a fastening tape tab would typically be releasably attached by the user. The mating loop region is located on the diaper end opposite the diaper end where the hook portion is located.

Although adhesive based closure systems and mechanical closure systems are generally satisfactory, a need remains for improved comfort and flexibility in products using such closure systems.

SUMMARY OF THE INVENTION

The difficulties and drawbacks associated with previously known systems are addressed in the present closure system and products using such.

In one aspect, the present invention provides a diaper having a front waist region, a rear waist region, a crotch region extending between the front waist region and the rear waist region, a topsheet, a backsheet, and an absorbent core disposed between the topsheet and the backsheet, and at least one fastener tab extending outward from beyond one of the front waist region and the rear waist region. The fastener tab includes a region of spunlace nonwoven material.

In another aspect, the present invention provides a fastener tab defining a first end and a second end, and a first face and a second face oppositely directed from the first face. The fastener tab comprises at least one region on at least one of the first face and the second face of a plurality of loop members. The loop members are in the form of a spunlace material.

In yet another aspect, the present invention provides a fastener tab defining a first end, a second end opposite from the first end, a first face extending between the first end and the second end, and a second face oppositely directed from the first face and extending between the first end and the second end. The fastener tab comprises a region of pressure sensitive adhesive disposed on the first face of the tab. The fastener tab also comprises a plurality of hook members disposed on the first face of the tab. And, the fastener tab comprises a plurality of loop members disposed on the second face of the tab, the loop members provided by a spunlace nonwoven material.

In still another aspect, the present invention provides a method of improving softness of a fastener tab using hook and loop members. The method comprises providing a fastener tab that includes at least one region with a plurality of hook members and at least one region with a plurality of loop members. The loop members are in the form of a spunlace material.

In yet another aspect, the present invention provides a method of releasably attaching a first member to a second member. The method comprises providing a plurality of hook members on the first member. The method also comprises providing a plurality of loop members on the second member. The plurality of loop members are in the form of a spunlace material. The method also comprises engaging the plurality of hook members with the spunlace material to thereby releasably attach the first member to the second member.

In still a further aspect, the present invention provides use of a spunlace material in a releasable closure system. In certain versions, the releasable closure system is a hook and loop fastener system and the spunlace nonwoven material serves as a plurality of loop members.

As will be realized, the invention is capable of other and different embodiments and its several details are capable of modifications in various respects, all without departing from the invention. Accordingly, the drawings and description are to be regarded as illustrative and not restrictive.

DETAILED DESCRIPTION OF THE EMBODIMENTS

The present invention relates to the use of certain nonwoven materials in a closure member such as disposed along a face of a fastener tab, as may be used in products such as disposable diapers. The closure member is typically a component of a releasable closure system such as a hook and loop fastener system. A fastener tab typically carries "hook" members which, in the case of a disposable diaper appropriately positioned about a baby, engage "loop" members along a strip of material on the front of the diaper in a region termed a "landing zone". In certain applications, a nonwoven backsheet material on the front of the diaper constitutes the landing zone.

In accordance with the present invention, generally, one or more fastener tabs adapted for use in a diaper are provided that include a particular type of nonwoven material along a face or side of the tab. The nonwoven material is exposed along a face of the tab that is opposite the face of the tab which typically contains the hooks. The nonwoven material serves as the loop members. This arrangement provides increased surface area for engagement between hook and loop members when one or more fastener tabs overlap another fastener tab. Overlapping fastener tabs typically occur when using a diaper for small infants. In such instances, the hooks along one face of a first fastener tab are engaged with loops in the landing zone on the front of the diaper. The second fastener tab is then laid over and upon the nonwoven material on an exposed face of the first fastener tab. The hooks of the second tab engage the nonwoven material of the first fastener tab.

It is known in the prior art to use nonwoven spunbond materials in fastener tabs for diapers. Specifically, in accordance with the invention, such nonwoven spunbond materials are replaced with a particular type of nonwoven material and one having certain characteristics. That material is a nonwoven spunlace material. An advantage of spunlace nonwovens is increased softness, thereby improving the comfort of diapers and other products using such materials. It has also been discovered that fastener tabs using spunlace materials typically provide greater flexibility than fastener tabs using spunbound materials. Improved flexibility promotes ease of use and engagement with other closure members.

A preferred spunlace nonwoven material includes polypropylene fibers, polyester fibers, either by themselves and/or combination, with other fibers and other materials. The use of polyester fibers is advantageous, particularly with polypropylene nonwoven materials because when performing further processing, the polyester fibers will not melt or otherwise detrimentally bond with the polypropylene fibers. This leads to a softer and more flexible material and in many applications, one that exhibits improved engagement properties with hook members.

Another advantage of the present invention is that in many applications, it may be possible to avoid the use of an adhesive on the tab. In certain applications, it is preferred that the fastener tabs are free of exposed regions of adhesive along the faces of the fastener tab. This configuration can reduce costs associated with the closure system. However, it will be appreciated that the present invention includes the use of spunlace materials in combination with one or more adhesives. That is, the invention includes fastener tabs and related closure systems using both spunlace nonwoven(s) as loop members in combination with one or more exposed regions of adhesives. Examples of suitable adhesives include but are not limited to pressure sensitive adhesives.

Generally, the present invention provides an improved fastener tab, a fastener tab using a particular nonwoven material, and a product such as a diaper having the noted fastener tab(s). More specifically, the present invention provides a fastener tab either singly or in multiples, and further provides such fastener tabs in roll or stock form, and/or incorporated in a consumer product such as disposable diapers, adult incontinence briefs, training pants, sanitary napkins and the like. These and other aspects are all described in greater detail herein.

Fastener Tab

The preferred embodiment fastener tabs are generally in the form of strips having a first face and a second oppositely directed second face. A region of material including a plurality of hook members extends along one of the first and second faces. And a region of a nonwoven material including a plurality of loop members extends along the other face. The material constituting the hook members may extend along the entirety or only a portion of the face of the tab. And, the nonwoven material constituting the loop members may extend along the entirety or only a portion of the other face of the tab.

Materials providing hook and loop members are well known in the art. And, a wide array of configurations and constructions are known for hooks and loops. For example, extensive information pertaining to hook and loop members and materials is set forth in U.S. Pat. Nos. 5,053,028; 5,176,670; 5,860,964; 6,146,369; and 6,524,294.

In a particularly preferred aspect, the fastener tab includes a spunlace nonwoven material. This spunlace nonwoven material constitutes and serves as the plurality of loop members.

The fastener tab may also include one or more regions of an adhesive exposed along portions of one or both faces of the tab. The adhesive is preferably a pressure sensitive adhesive. Details as to pressure sensitive adhesives such as used in conjunction with closure systems in diaper products are set forth in U.S. Pat. Nos. 4,369,786; 4,795,456; 5,462,540; 5,599,620; 5,660,659; 5,720,739; and 6,419,667.

Spunlace Nonwovens

A well known technique for consolidating fibers in a web is mechanical bonding, which entangles the fibers to give strength to a web. In mechanical bonding, a widely used method is spunlacing or hydroentanglement. Spunlacing uses high-speed jets of water directed to strike a fibrous web so that the fibers entangle about one another. As a result, nonwoven fabrics made by this method have specific properties, such as for example, soft handling and drapability.

Spunlacing is performed typically by entangling a web of loose fibers on a porous belt or moving a perforated or patterned screen to form a sheet structure by subjecting the fibers to multiple rows of fine high-pressure jets of water.

The formed web, usually air-laid or wet-laid, but sometimes spun bond or melt-blown, etc., is first compacted and prewetted to eliminate air pockets and then water-needled. The water pressure generally increases from the first to the last injectors. Pressures as high as 2200 psi are used to direct the water jets onto the web. This pressure is sufficient for most nonwoven fibers, although higher pressures are used in specialized applications. Injector hole diameters range from about 100 to about 120 mm and the holes are typically arranged in rows with from about 3 to about 5 mm spacing, with one row typically containing 30 to 80 holes per 25 mm. The impinging of the water jets on the web causes the entanglement of fibers. The jets impart most of the kinetic energy primarily in rearranging fibers within the web and, secondly, in rebounding against the substrates, thereby dissipating energy to the fibers. A vacuum within the roll removes water from the product, thereby preventing flooding of the product and reduction in the effectiveness of the jets to move the fibers and cause entanglement.

Usually, hydroentanglement is applied on both sides in a step-wise manner. Typically, a first entanglement roll acts on the first side a number of times in order to impart to the web the desired amount of bonding and strength. The web then passes over a second entanglement roll in a reverse direction in order to treat and, thereby, consolidate the other side of the fabric. The hydroentangled product is then passed through a dewatering device where excess water is removed and the fabric is dried.

Hydroentanglement can be carried out using dry-laid (carded or air-laid) or wet-laid webs as a precursor. Most commonly, fibrous web precursors are mixtures of cellulose and fibers of poly(ethylene terephthalate) (PET), nylon, acrylics, Kevlar (P84, (imide) etc.

In general, cellulosic fibers may be preferred for certain applications due to their high strength, pliability, plastic deformation resistance and water insolubility. Cellulosic fibers are hydrophilic, chemically stable and relatively colorless. Another advantage is that cellulose has an inherent bonding ability caused by a high content of hydroxyl groups, which attract water molecules. As the water evaporates from the fabric, the hydroxyl groups on fiber surface link together by hydrogen bonds.

Fiber selection is typically governed by the following considerations. Fibers with low bending modulus require less entangling energy than those with high bending modulus. For a given polymer type, larger diameter fibers are more difficult to entangle than smaller diameter fibers because of their greater bending rigidity. For PET, 1.25 to 1.5 deniers are typically used. For a given polymer type and fiber denier, a triangular shaped fiber will have 1.4 times the bending stiffness of a round fiber. An extremely flat, oval or elliptical shaped fiber could have only 0.1 times the bending stiffness of a round fiber. Shorter fibers are more mobile and produce more entanglement points than longer fibers. Fabric strength, however, is proportional to fiber length. Therefore, fiber length is typically selected to give the best balance between the ratio of the number of entanglement points and fabric strength. For PET, the fiber length is typically such that this ratio is from 1.8 to 2.4. Crimp is required in staple fiber processing systems and contributes to fabric bulk. Too much crimp can result in lower fabric strength and entanglement. Hydrophilic fibers entangle more easily than hydrophobic fibers because of the higher drag forces.

For certain embodiments of the invention, it is preferred to use polyester fibers or polyolefin fibers, and in particular applications, blends or combinations of these fibers. For example, it is preferred to use fibers of polypropylene, polyesters and combinations of such materials. Another fiber type contemplated for use in spunlace materials suitable for the invention is viscose fibers. Viscose fibers are synthetic fibers made of thin filaments of regenerated cellulose, extruded from a solution of viscose. Viscose fibers are also referred to as viscose rayon fibers. The preferred fastener materials and tabs can utilize combinations of any of these fibers.

Spunlaced fabrics exhibit high drape, softness and comfortableness in handling because more fiber entanglement leads to increased strength without an increase in shear modulus. It has also been shown that there is a relationship between absorbency capacity and hydroentangling energy used. An increase of hydroentangling energy results in a decrease of absorbency capacity and absorbency rate. Shear modulus remains low and is virtually independent of the degree of entanglement. The softness of the fabric is explained by the fact that the entangled structures are more compressible than bonded ones, as well as having mobility and partial alignment of fibers in the thickness direction. The absence of a binder is seen to result in a fabric with yarn-like fabric intersections. The intersections are more highly interconnected than yarns of conventional fabrics because individual fibers can migrate from one fabric intersection to another. This tends to stabilize the resulting structure. This structure appears to be the reason for good dimensional stability, which is also accountable for drape, softness, and good strength/weight properties of the fabric, pilling and abrasion behavior. Therefore, in a preferred aspect of the invention, the spunlace material used in one or more fastener tabs is free of any regions at which fibers are bonded by having been melted together. This feature is referred to herein as "free of melt bonded intersections." Spunlace materials that are free of melt bonded intersections have been found to exhibit remarkable softness, feel, perceived quality, aesthetics, and other desirable properties.

A nonwoven spunlace material is distinguishable from conventional nonwoven and non-spunlace materials. First, a nonwoven spunlace material has a plurality of loop structures that are formed by entangling fibers without interbonding the fibers. This feature results in improved softness of the resulting spunlace material. Other types of nonwoven materials use some type of bonding in the fiber structure to form the loops, for example by bonding the fibers together at their intersections or a portion of their intersections, or by bonding the fibers to a substrate or other backing. Again, spunlace nonwoven materials are characterized as being free of any bonding between fibers. Instead, the fibers of spunlace nonwoven materials are interlocked in a fibrous structure by mechanical intertwining occurring during entanglement and preferably during hydroentanglement.

The strength of hydroentangled fabrics is typically lower than that of woven and higher than that of knitted fabrics, whereas the wash durability is considerably lower than that of woven or knitted fabrics Although not wishing to be limited to any particular characteristic of the spunlace material, a primary parameter is basis weight. A preferred range for the basis weight is from about 15 grams per square meter (gsm) to about 60 gsm, and more preferably from about 25 gsm to about 45 gsm.

Representative examples of commercially available spunlace materials include but are not limited to those available under the designation SAWATEX from Sandler, AG; AQUADIM from Tharreau Industries of France; and HY-JET from RKW SE of Germany.

In a particularly preferred however non-limiting aspect, the present invention provides a fastener tab having a region of hook members and a region of a particular grade of spunlace material which is free of melt bonded intersections, is formed by hydroentanglement which thereby produces a mechanically intertwined fibrous matrix having a basis weight of from about 25 gsm to about 45 gsm, and which exhibits enhanced softness as compared to a comparable nonwoven material however one that is not a spunlace material.

Diapers

A typical disposable diaper comprises a front waist region, a rear waist region, a crotch region extending between the front waist region and the rear waist region, a liquid-pervious topsheet, a liquid-impervious backsheet, and an absorbent core disposed between the topsheet and the backsheet. Generally, the topsheet and the backsheet extend outward longitudinally beyond longitudinally opposite ends of the absorbent core and are secured together in the front waist region and the rear waist region, respectively, so as to form a pair of end flaps in each of the front waist region and the rear waist region. At least one strip of fastener tabs or hook and loop tape according to the preferred embodiments are attached to the backsheet between one pair of the end flaps. A tab is preferably attached to each of the other pair of end flaps on the backsheet, each tab having a plurality of hooks which are formed thereon and face the topsheet.

Several preferred embodiments in accordance with the present invention are described as follows.

Figure 1:
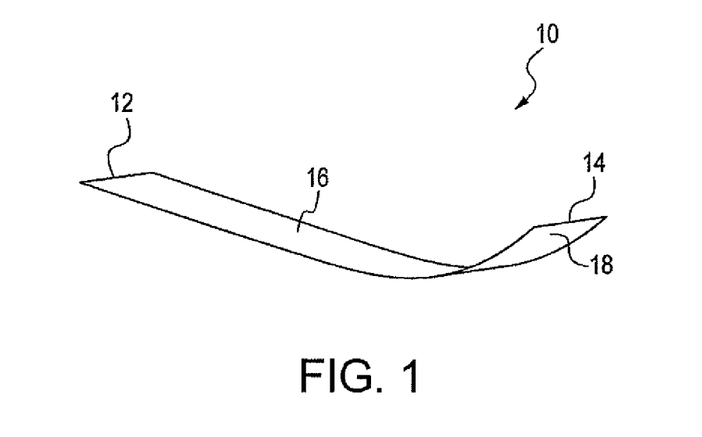
FIG. 1 is a perspective schematic view of a preferred embodiment fastener tab in accordance with the invention.

FIG. 1 illustrates a preferred embodiment fastener tab 10 in accordance with the invention. The fastener tab 10 generally defines a first end 12 and a second end 14. The fastener 10 also defines a first face 16 and an oppositely directed second face 18. The tab 10 comprises a plurality of hook members disposed along one or more of the faces 16 and 18. And, the tab 10 comprises a plurality of loop members disposed along one or more of the faces 16 and 18. Preferably, the hook members are disposed on the first face 16 and the loop members are disposed along the second face 18.

The hook and loop members can be provided along the faces in nearly any manner. Preferably a material providing the hook member is disposed along the first face 16, and a material providing the loop members 18 is disposed along the second face 18. Most preferably, the material providing the loop members is the form of a spunlace material.

The spunlace material can be provided along the entirety or along a portion of a face of the tab 10. Although it is preferred to provide the spunlace material on only one face, such as the second face 18 of the tab 10, it is contemplated that such material can be provided along both faces 16 and 18.

The fastener tab 10 may also include one or more regions of an adhesive exposed along portions of one or both faces 16 and 18. The adhesive is preferably a pressure sensitive adhesive.

Figure 2:
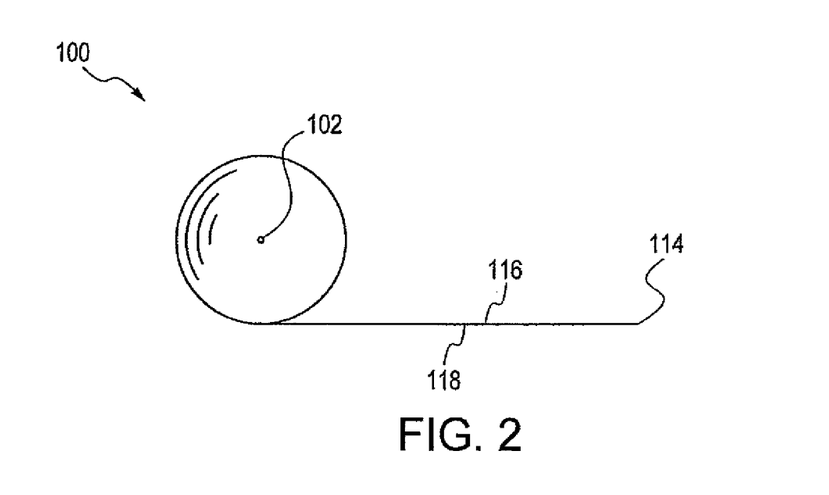
FIG. 2 is a side schematic view of a preferred embodiment roll of fastener material in accordance with the invention.

FIG. 2 illustrates a preferred embodiment fastener material 100, existing in a roll form. One or more individual fastener tabs such as tab 10 depicted in FIG. 1 can be cut or formed from the roll of fastener material 100 shown in FIG. 2. The fastener tab 10 of FIG. 1 is an example of a strip of fastener material. The roll of fastener material in FIG. 2 includes a relatively long section of fastener material wound about a center 102. The fastener material 100 defines faces 116 and 118 corresponding to previously described faces 16 and 18. The fastener material defines a first end (not shown) at the center 102 and a distal or loose end 114.

The width of the roll of fastener material of the present invention depends on the intended application. Typically, the rolls that are used for closure tabs for disposable articles have a width in the range of about 30 to about 100 mm. In one embodiment, the width of the rolls is in the range of about 50 to about 70 mm. The closure tape can be provided in a roll, for example, as a disc wound roll or a spool wound roll. The fastener material can be wound up to a stable roll, i.e., a roll that can be unwound continuously and at a high speed so that a closure tab can be cut therefrom without telescoping of the roll.

Figure 3:
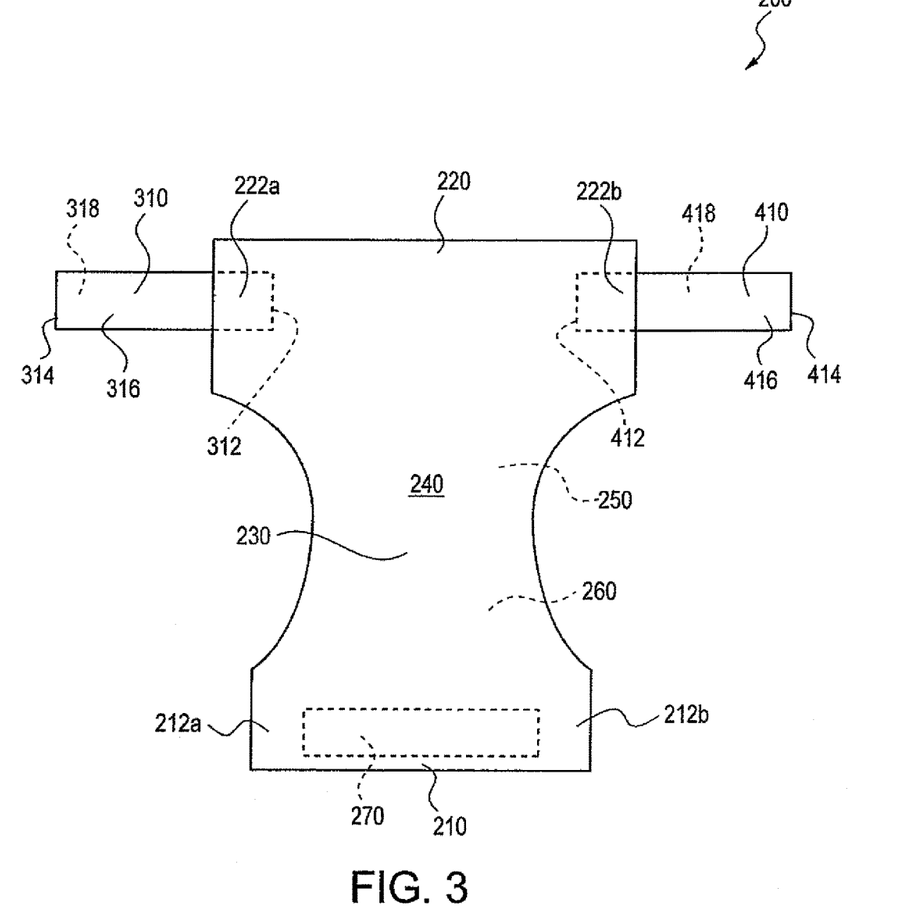
FIG. 3 is a schematic view of a preferred embodiment diaper in accordance with the invention.
Figure 4:
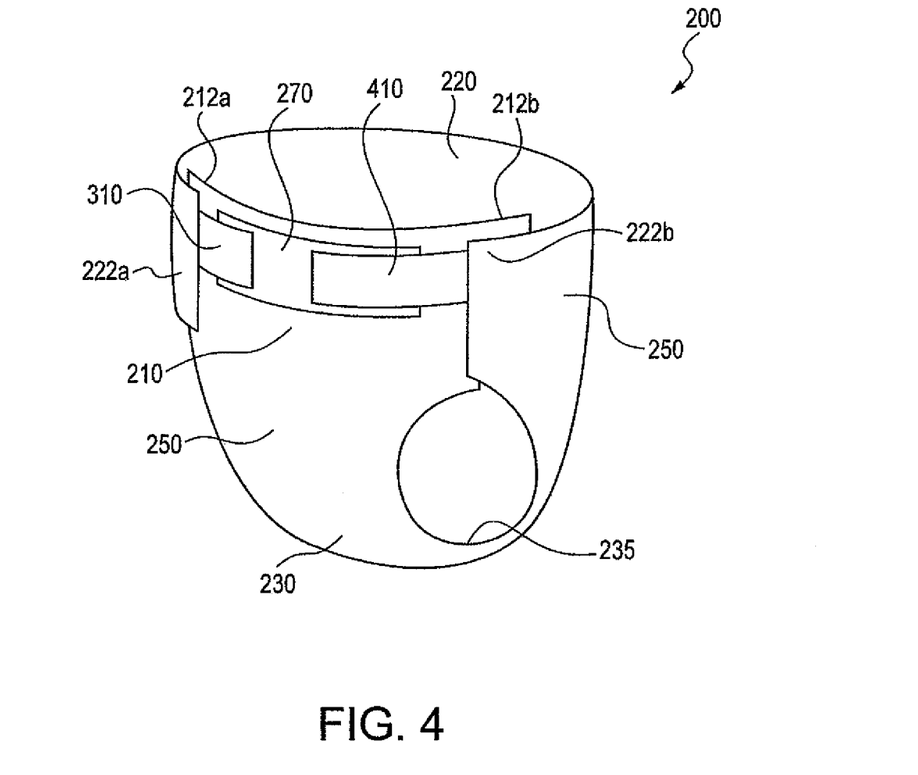
FIG. 4 is a perspective schematic view of the preferred diaper depicted in FIG. 3 in a fastened state.

FIGS. 3 and 4 schematically illustrate a preferred embodiment diaper 200 using two preferred fastener tabs as described herein. The preferred diaper 200 comprises a front waist region 210, a rear waist region 220, a crotch region 230 extending therebetween, a liquid-pervious topsheet 240, a liquid-impervious backsheet 250, and an absorbent core 260 disposed between the topsheet 240 and the backsheet 250. The diaper 200 includes a pair of end flaps along each front and rear region. Thus, the diaper 200 includes a front pair of end flaps 212a and 212b along the front waist region 210. And, the diaper 200 includes a rear pair of end flaps 222a and 222b along the rear waist region 220. The end flaps can be elastic and similar to elastic side panels. The end flaps may also be non-elastic. At least one region of material providing hook members or loop members is provided on the backsheet 250 and preferably between a pair of the end flaps. Preferably, a region of such material depicted as 270 in FIGS. 3 and 4 is provided on the backsheet 250 between the front end flaps 212a and 212b. The material 270 is also known as a landing zone for fastener tabs described in greater detail herein.

The preferred diaper 200 preferably includes a first fastener tab 310 and a second fastener tab 410. Each tab 310 and 410 corresponds to the previously described fastener tab 10 depicted in FIG. 1. Each tab extends outward from beyond the front waist region or the rear waist region. More specifically, the fastener tab 310 includes a first end 312 and a second end 314, and first and second faces 316 and 318 extending between the ends 312 and 314. And, the fastener tab 410 includes a first end 412 and a second end 414, and first and second faces 416 and 418 extending between the ends 412 and 414.

With further reference to FIGS. 3 and 4, preferably the first faces 316 and 416 of the tabs 310 and 410 respectively, include one or more exposed regions of hook members. And, preferably the second faces 318 and 418 of the tabs 310 and 410 respectively, include one or more exposed regions of loop members. And, preferably, the landing zone 270 includes one or more regions of loop members. As described herein, preferably, the materials providing the loop members is a spunlace nonwoven material. Most preferably, the fastener 310 includes a spunlace nonwoven material along the second face 318. And preferably, the fastener 410 includes a spunlace nonwoven material along the second face 418. The spunlace material(s) are preferably as described herein and include polyolefin fibers and most preferably polypropylene fibers and/or polyester fibers. The spunlace nonwoven material used in the tabs 310 and 410 is preferably free of melt bonded intersections.

Referring to FIG. 4, the diaper 200 is illustrated in a fastened state, such as when positioned about a baby or user (not shown). As will be understood, upon positioning the front and rear waist regions 210 and 220, respectively, toward one another and thereby folding the diaper 200 along the crotch region 230, the rear end flaps 222a, 222b are each generally laid upon the front end flaps 212a, 212b. Leg openings such as opening 235 are thereby formed by the diaper 200. The fastener tab 310 extending from the rear end flap 222a is engaged with a region of the landing strip 270. And, a fastener tab 410 extending from the rear end flap 222b is engaged with a region of the landing strip 270. Specifically, the first faces 316 and 416 containing hook members of the fastener tabs 310 and 410 are contacted and engaged with the loop members within the landing zone 270.

Figure 5:
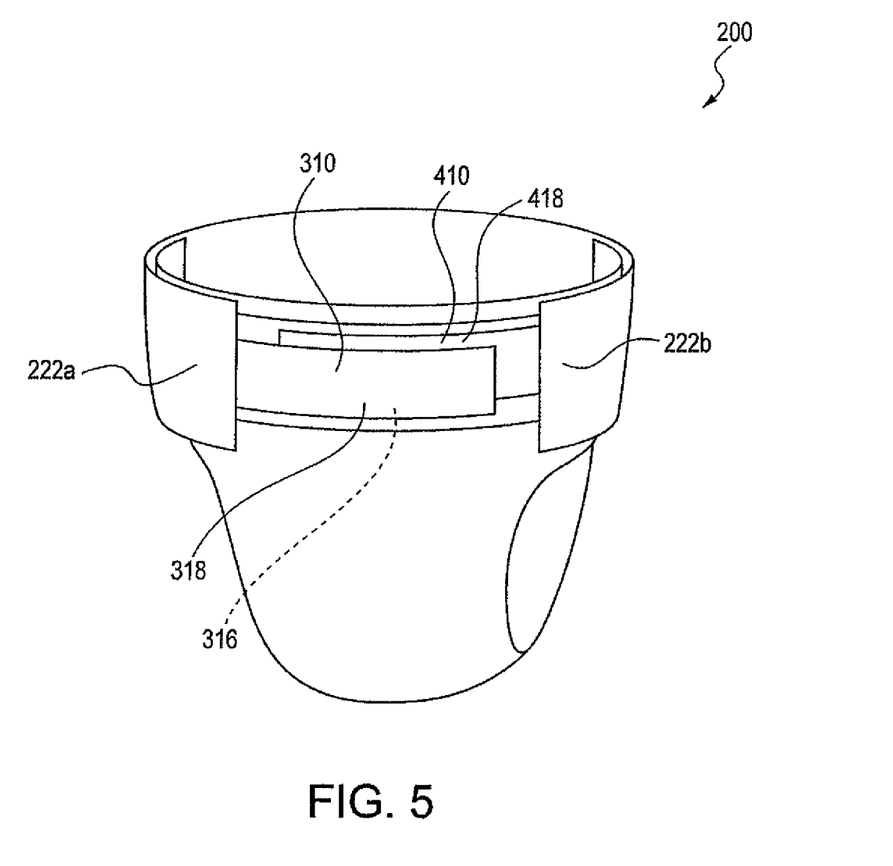
FIG. 5 is a perspective schematic view of the preferred diaper depicted in FIG. 3 in another fastened state.

FIG. 5 illustrates the preferred embodiment diaper 200 in yet another fastened state, however such that the span of the diaper about the waist region is relatively small or at least smaller than that depicted in FIG. 4. Examples of such fastened states include when positioning the diaper about an infant or small baby. In such applications, it is typically necessary to overlap one of the fastener tabs with the other fastener tab. Such overlapping may be of the entire tab or of only a portion of a tab. FIG. 5 illustrates an example of the fastener tab 310 partially overlapping the fastener tab 410, and specifically, a portion of the first face 316 of the fastener 310 having a plurality of hook members contacting and engaging a portion of the second face 418 of the fastener 410 having a plurality of loop members provided by a spunlace nonwoven material.

Figure 6:
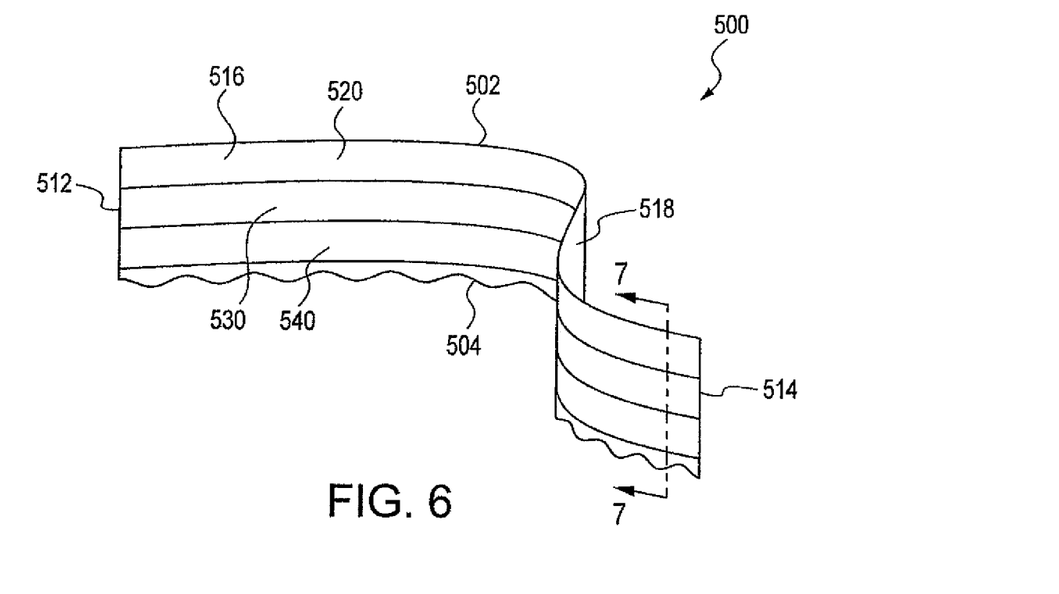
FIG. 6 is a perspective schematic view of another preferred embodiment fastener tab in accordance with the invention.
Figure 7:
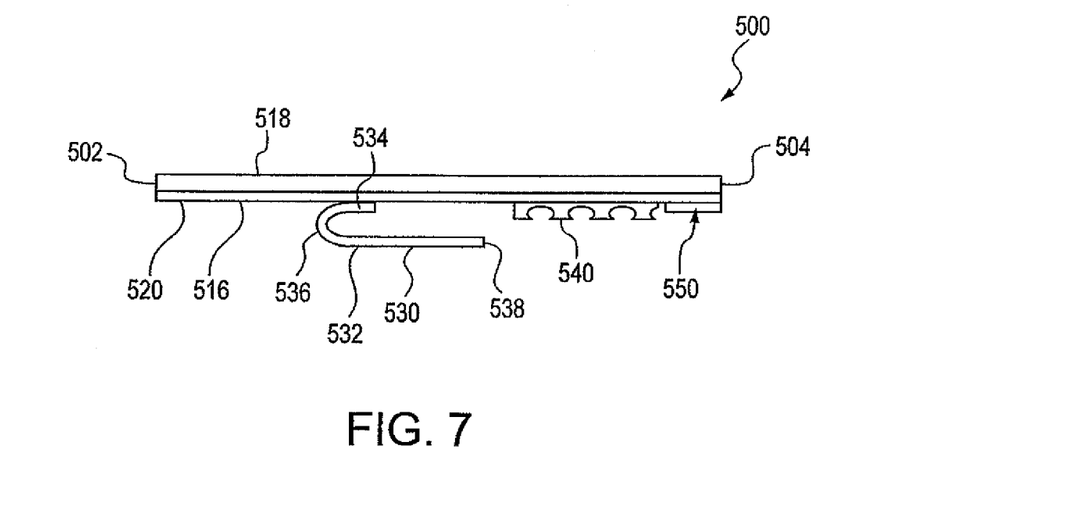
FIG. 7 is a cross sectional schematic view of the fastener tab depicted in FIG. 6, taken across line 7-7.

FIGS. 6 and 7 illustrate another preferred embodiment fastener tab 500 in accordance with the present invention.

The tab 500 defines a first end 512, a second opposite end 514, a first edge 502 extending between the ends 512 and 514, and a second edge 504 opposite from the first edge 502 and also extending between the ends 512 and 514. The tab 500 also defines a first face 516 and an oppositely directed second face 518. One or more or both of the faces 516 and 518 may define one or more region(s) of pressure sensitive adhesive(s), and one or more region(s) of material providing a plurality of hook members. For example, the tab 500 is shown as including (i) a first region 520 of a pressure sensitive adhesive, (ii) a second region 530 of a pressure sensitive adhesive, and (iii) a region 540 of a material providing a plurality of hook members along the face 516. And the tab 500 further includes a spunlace nonwoven material along the entirety or substantially so, of the second face 518. The invention also includes versions of the fastener tab 500 in which the spunlace nonwoven material is disposed on only a portion of the second face 518. The pressure sensitive adhesive(s) used in the regions 520 and 530 may be the same or different from one another. As will be understood, the invention includes a wide assortment of alternative configurations such as varied arrangements of the regions of pressure sensitive adhesive(s), regions of hook members, and regions of loop members. In the preferred embodiment tab 500, it is preferred that the regions 520, 530, and 540 generally extend completely between the ends 512 and 514. However, the invention includes alternative configurations in which one or more of the regions is discontinuous.

Referring further to FIG. 7, a schematic cross sectional view taken along line 7-7 of the fastener in FIG. 6 is presented. Preferably, the second region 530 of a pressure sensitive adhesive is in the form of a layer 532 bonded along a secured edge 534 and folded at region 536 and extending to a free edge 538. The layer 532 is preferably in the form of a polymeric or paper film having a pressure sensitive adhesive disposed along at least an exposed region of the layer 532. An optional edge layer 550 is preferably disposed along the second edge 504 on the first face 516.

Methods

In various embodiments of the invention, methods of improving softness, feel, perceived quality, aesthetics, and other characteristics of a fastener tab and/or diaper using such fastener tab, are provided. The methods involve using a spunlace material as a collection or plurality of loop members in a releasable closure system such as a hook and loop fastener system. In one embodiment, a method of improving softness of a fastener tab using hook and loop members is provided. The method comprises providing a fastener tab that includes at least one region having a plurality of hook members and at least one region having a plurality of loop members. The loop members are in the form of a spunlace material. The preferred materials and basis weights of the spunlace material are as previously described herein. The spunlace material is preferably free of melt bonded intersections.

In another embodiment, a method of releasably attaching a first member to a second member is provided. The members may be any component, article, substrate or region of a component, article or substrate. In certain versions, the first member is one region of a fastener and the second member is another region of the fastener. However, it will be appreciated that in no way is the invention limited to such. The methods comprise providing a plurality of hook members on the first member. The methods also comprise providing a plurality of loop members on the second member in which the plurality of loop members are in the form of a spunlace material. The method also comprises engaging the plurality of hook members with the spunlace material to thereby releasably attach the first member to the second member. The preferred materials and basis weights of the spunlace material are as previously described herein. The spunlace material is preferably free of melt bonded intersections.

Use Aspects

In still other embodiments of the invention, spunlace nonwoven materials are used in a releasable closure system. The releasable closure system is preferably a hook and loop fastener system. The spunlace material preferably serves as a plurality of loop members. The preferred materials and basis weights of the spunlace material are as previously described herein. The spunlace material is preferably fee of melt bonded intersections. In certain embodiments herein, the spunlace material is formed by hydroentanglement.

Many other benefits will no doubt become apparent from future application and development of this technology.

All patents, published applications, and articles noted herein are hereby incorporated by reference in their entirety.

It will be understood that any one or more feature or component of one embodiment described herein can be combined with one or more other features or components of another embodiment. Thus, the present invention includes any and all combinations of components or features of the embodiments described herein.

As described hereinabove, the present invention solves many problems associated with previous type products and related methods. However, it will be appreciated that various changes in the details, materials and arrangements of parts or components, which have been herein described and illustrated in order to explain the nature of the invention, may be made by those skilled in the art without departing from the principle and scope of the invention, as expressed in the appended claims.

What is claimed is:

1. A fastener tab defining a first end, a second end opposite from the first end, a first face extending between the first end and the second end, and a second face oppositely directed from the first face and extending between the first end and the second end, the fastener tab comprising:
   a region of exposed pressure sensitive adhesive disposed on the first face of the tab;
   a plurality of hook members disposed on the first face of the tab; and
   a plurality of loop members disposed on the second face of the tab, the loop members provided by a spunlace nonwoven material.

2. The fastener tab of claim 1 wherein the spunlace material comprises at least one fiber selected from the group consisting of polyolefin fibers, polyester fibers, and combinations thereof.

3. The fastener tab of claim 2 wherein the polyolefin fibers are polypropylene fibers.

4. The fastener tab of claim 1 wherein the spunlace material is free of melt bonded intersections.

5. The fastener tab of claim 1 wherein the region of pressure sensitive adhesive is a first region of adhesive, the fastener tab further comprising:
   a second region of pressure sensitive adhesive disposed on the first face of the tab.

6. The fastener tab of claim 1 wherein the spunlace material has a basis weight of from about 15 gsm to about 60 gsm.

7. The fastener tab of claim 1 wherein the spunlace material has a basis weight of from about 25 gsm to about 45 gsm.

\* \* \* \* \*